United States Patent
Matsuta et al.

(10) Patent No.: US 12,410,112 B2
(45) Date of Patent: Sep. 9, 2025

(54) PURIFICATION METHOD FOR FLUOROOLEFIN HAVING STRUCTURE OF =CF$_2$ OR =CHF, HIGH-PURITY FLUOROOLEFIN, AND PRODUCTION METHOD THEREFOR

(71) Applicant: KANTO DENKA KOGYO CO., LTD., Tokyo (JP)

(72) Inventors: Yuka Matsuta, Gunma (JP); Korehito Kato, Gunma (JP)

(73) Assignee: KANTO DENKA KOGYO CO., LTD., Tokyo (JP)

( * ) Notice: Subject to any disclaimer, the term of this patent is extended or adjusted under 35 U.S.C. 154(b) by 422 days.

(21) Appl. No.: 17/641,262

(22) PCT Filed: Sep. 11, 2020

(86) PCT No.: PCT/JP2020/034442
§ 371 (c)(1),
(2) Date: Mar. 8, 2022

(87) PCT Pub. No.: WO2021/049605
PCT Pub. Date: Mar. 18, 2021

(65) Prior Publication Data
US 2022/0281785 A1 Sep. 8, 2022

(30) Foreign Application Priority Data
Sep. 12, 2019 (JP) ................. 2019-166611

(51) Int. Cl.
*C07C 17/389* (2006.01)
(52) U.S. Cl.
CPC ................. *C07C 17/389* (2013.01)
(58) Field of Classification Search
CPC ................................ C07C 17/389
See application file for complete search history.

(56) References Cited

U.S. PATENT DOCUMENTS

| | | |
|---|---|---|
| 6,544,319 B1 | 4/2003 | Krouse et al. |
| 9,012,703 B2 | 4/2015 | Sharratt et al. |
| | (Continued) | |

FOREIGN PATENT DOCUMENTS

| | | |
|---|---|---|
| CN | 102887812 A | 1/2013 |
| CN | 103449959 A | 12/2013 |
| | (Continued) | |

OTHER PUBLICATIONS

Ambiter "1, 1,3,3,3-pentafluoropropene" Deposit and available date May 5, 2018 (Year: 2018).*
ISR of PCT/JP2020/034442, dated Oct. 13, 2020.

*Primary Examiner* — Medhanit W Bahta
(74) *Attorney, Agent, or Firm* — Dority & Manning, P.A.

(57) ABSTRACT

Impurities are removed from a fluoroolefin having a structure of =CF$_2$ or =CHF that has been obtained by a dehydrohalogenation reaction and that contains haloalkene, haloalkane, and/or haloalkyne impurities.
Provided are: a method of purifying a fluoroolefin having a structure of =CF$_2$ or =CHF, comprising bringing a fluoroolefin having a structure of =CF$_2$ or =CHF that has been obtained by a dehydrohalogenation reaction and that contains at least one of haloalkane, haloalkene, and/or haloalkyne impurities into contact with a solid adsorbent to remove the impurities through adsorption; a high-purity fluoroolefin; and a production method therefor.

12 Claims, 1 Drawing Sheet

(56) References Cited

U.S. PATENT DOCUMENTS

| | | |
|---|---|---|
| 2006/0094911 A1 | 5/2006 | Rao et al. |
| 2011/0105809 A1* | 5/2011 | Devic .................. C07C 17/389 |
| | | 570/179 |
| 2012/0203037 A1* | 8/2012 | Sharratt ................ C07C 17/389 |
| | | 570/179 |
| 2014/0305161 A1 | 10/2014 | Kawaguchi |
| 2015/0259267 A1* | 9/2015 | Sun ........................ C07C 17/25 |
| | | 570/155 |
| 2016/0347693 A1 | 12/2016 | Fukushima et al. |

FOREIGN PATENT DOCUMENTS

| | | |
|---|---|---|
| EP | 1278714 B1 | 1/2005 |
| EP | 3904320 A1 | 11/2021 |
| JP | 1989040436 U | 10/1990 |
| JP | 2002226411 A | 8/2002 |
| JP | 2003261480 A | 9/2003 |
| JP | 2006193437 A | 7/2006 |
| JP | 2008518938 A | 6/2008 |
| JP | 4121745 B2 | 7/2008 |
| JP | 2011136955 A | 7/2011 |
| JP | 2012001495 A | 1/2012 |
| JP | 2013508265 A | 3/2013 |
| JP | 2013241389 A | 12/2013 |
| JP | 2013241390 A | 12/2013 |
| JP | 6074454 B2 | 2/2017 |
| JP | 2017196601 A | 11/2017 |
| JP | 2020105135 A | 7/2020 |
| KR | 20100082618 A | 7/2010 |
| WO | 2013099856 A1 | 7/2013 |
| WO | 2013151070 A1 | 10/2013 |
| WO | 2015125877 A1 | 8/2015 |

* cited by examiner

PURIFICATION METHOD FOR FLUOROOLEFIN HAVING STRUCTURE OF =CF$_2$ OR =CHF, HIGH-PURITY FLUOROOLEFIN, AND PRODUCTION METHOD THEREFOR

TECHNICAL FIELD

The present invention relates to a purification method for a fluoroolefin having a structure of =CF$_2$ or =CHF, a high-purity fluoroolefin, and a production method therefor.

BACKGROUND ART

Due to the low values of ODP (ozone depletion potential) and GWP (global warming potential), hydrofluoroolefins (HFOs) are known as desirable alternatives to HCFCs. For example, 1,1,3,3,3-pentafluoropropene is known as a compound useful as a refrigerant, heat transfer fluid, fire extinguishing agent, propellant, blowing agent, inflating agent, gas derivative, polymerization medium, or monomer.

It is known that 1,1,3,3,3-pentafluoropropene is obtained by dehydrohalogenation reactions. For example, Patent Literature (PTL) 1 discloses a process for manufacturing 1,1,3,3,3-pentafluoropropene by pyrolyzing 1,1,1,3,3,3-hexafluoropropane in the absence of a catalyst. PTL 1 explains in [0002] that the pyrolysis of a raw material gas at a high temperature produces complex mixtures which are difficult to separate. Meanwhile, PTL 1 also discloses in [0007] that the 1,1,3,3,3-pentafluoropropene (CF$_3$CH=CF$_2$) product is stable and does not undergo further conversion to products containing fewer hydrogen and/or fluorine atoms. For this reason, PTL 1 lacks a description about impurities, which were raised as a problem when the present inventors conducted studies.

For the use as a refrigerant, heat transfer fluid, fire extinguishing agent, propellant, blowing agent, inflating agent, gas derivative, polymerization medium, or monomer, it is required to reduce easily and efficiently the content of haloalkanes and haloalkenes bonded with a chlorine atom or a fluorine atom that have been formed as by-products.

Such haloalkanes and haloalkenes have a boiling point close to the boiling point (about −21° C.) of 1,1,3,3,3-pentafluoropropene and thus make the separation through distillation difficult. Consequently, a distillation apparatus with numerous stages is required to reduce the content, thereby constituting problems with mass production, such as increasing equipment costs.

As for tetrafluoropropene, which is particularly difficult to separate, a distillation column with the minimum number of theoretical stages of 113 is required to obtain 1,1,3,3,3-pentafluoropropene of 99.99% or more in purity according to the investigation by the present inventors.

Concerning purification methods through adsorption, PTL 2 discloses a method of bringing a fluid containing a fluoroolefin and alkanes having a carbon number of 1 into contact with synthetic zeolite 4A, thereby removing the alkanes having a carbon number of 1. PTL 3 discloses a process for removing at least one (hydro)haloalkene impurity by contacting at a temperature of −20° C. to 100° C. with a solid adsorbent (zeolite) having a pore opening of 7 to 10 Å as the largest dimension. PTL 4 discloses a process of contacting 2,3,3,3-tetrafluoropropene containing (hydro)halocarbon compounds with an aluminium-containing adsorbent, activated carbon, or a mixture thereof. PTL 5 discloses a method of bringing 1,1,1,3,3-pentafluoropropane containing halopropenes into contact with a solid adsorbent (particularly, activated carbon), thereby removing the halopropenes. PTL 6 discloses a purification method including bringing 2,3,3,3-tetrafluoropropene containing hydroalkene impurities and hydroalkane impurities with a molecular sieve having an effective pore size of 5 to 10 Å to remove the impurities at least partially. PTL 7 discloses a method of purifying a fluoroolefin by removing, through adsorption, impurities having a carbon number of 1 or 2 from a fluid mixture containing a fluoroolefin having a carbon number of 3 or more.

PTL 8 describes a molecular sieve (synthetic zeolite), silica gel, and activated alumina as dehydrating agents for the dehydration of a distillate withdrawn from a distillation column. PTL 9 discloses that 1,1,3,3,3-pentafluoropropene (1225zc) is difficult to separate from 3,3,3-trifluoropropene (1243zf) having a structure of =CH$_2$ due to the close boiling points and that 1225zc is separated from 1243zf by using an activated carbon adsorbent.

CITATION LIST

Patent Literature

PTL 1: Japanese Unexamined Patent Application Publication (Translation of PCT Application) No. 2008-518938
PTL 2: WO 2013/151070
PTL 3: Japanese Patent No. 4121745
PTL 4: Japanese Patent No. 6074454
PTL 5: Japanese Unexamined Patent Application Publication No. 2002-226411
PTL 6: Japanese Unexamined Patent Application Publication No. 2012-1495
PTL 7: Japanese Unexamined Patent Application Publication No. 2013-241390
PTL 8: WO 2013/099856
PTL 9: Japanese Unexamined Patent Application Publication (Translation of PCT Application) No. 2013-508265

SUMMARY OF INVENTION

Technical Problem

PTL 2 concerns a method of removing hydroalkanes having a carbon number of 1, and PTL 7 concerns a method of purifying a fluoroolefin by removing impurities having a carbon number of 1 or 2. PTL 3 and PTL 5 concern a process for removing (hydro)haloalkene impurities, which is a purification process from a saturated hydrofluorocarbon. PTL 4 and PTL 6 concern a method of removing hydrohaloalkane and hydrohaloalkene impurities contained in 2,3,3,3-tetrafluoropropene (1234yf) having a structure of =CH$_2$. As in the foregoing, there has been no known method of removing, through adsorption, impurities including haloalkanes and haloalkenes having a carbon number of 3 and hence having a further close boiling point.

When a fluoroolefin having a carbon number of 3 or more and a structure of =CF$_2$, such as 1,1,3,3,3-pentafluoropropene, is produced by the above-mentioned synthetic reaction under high-temperature conditions, for example, haloalkanes and haloalkenes having a carbon number of 3 and hence having a further close boiling point are formed as by-products in addition to haloalkanes having a carbon number of 1 and/or various haloalkanes and haloalkenes having a carbon number of 2. The studies by the present inventors revealed that efficient removal of haloalkane and haloalkene impurities having a carbon number of 3 and hence having a further close boiling point, in addition to haloalkanes having a carbon number of 1 and/or haloalkanes and haloalkenes having a carbon number of 2, is needed to obtain a target fluoroolefin having a carbon number of 3 or more at a yield as high as possible. However, there has been no known method of solely removing, through adsorption, undesirable haloalkane and haloalkene impurities having a carbon number of 3 from a mixture containing a fluoroolefin having a carbon number of 3 or more.

An object of the present invention is to provide a method of efficiently purifying a fluoroolefin having a structure of $=CF_2$ or $=CHF$ by removing, through adsorption, impurities including haloalkanes, haloalkenes, and haloalkynes having a close boiling point and thereby obtaining a fluoroolefin having a further high purity.

Solution to Problem

The present invention provides the following.

[1] A method of purifying a fluoroolefin having a structure of $=CF_2$ or $=CHF$, comprising bringing a fluoroolefin having a structure of $=CF_2$ or $=CHF$ that has been obtained by a dehydrohalogenation reaction and that contains at least one of haloalkane, haloalkene, and haloalkyne impurities into contact with a solid adsorbent to remove the impurities through adsorption.

[2] The method according to [1], where the solid adsorbent has an effective pore size of 3 to 50 Å.

[3] The method according to [1] or [2], where the solid adsorbent is at least one selected from the group consisting of activated carbon, molecular sieves of type A or type X, and activated alumina.

[4] The method according to any of [1] to [3], where the total content of the impurities in the fluoroolefin that contains the impurities is more than 0 ppm and 10 mass % or less.

[5] The method according to any of [1] to [4], where the fluoroolefin that contains the impurities is brought into contact with the solid adsorbent for a contact time of up to 60 minutes.

[6] A method of producing a high-purity fluoroolefin having a structure of $=CF_2$ or $=CHF$, comprising bringing a fluoroolefin having a structure of $=CF_2$ or $=CHF$ that has been obtained by a dehydrohalogenation reaction and that contains at least one of haloalkane, haloalkene, and haloalkyne impurities into contact with a solid adsorbent to remove the impurities through adsorption.

[7] The method according to [6], where the solid adsorbent has an effective pore size of 3 to 50 Å.

[8] The method according to [6] or [7], where the solid adsorbent is at least one selected from the group consisting of activated carbon, molecular sieves of type A or type X, and activated alumina.

[9] The method according to any of [6] to [8], where the total content of the impurities in the fluoroolefin that contains the impurities is more than 0 ppm and 10 mass % or less.

[10] The method according to any of [6] to [9], where the fluoroolefin that contains the impurities is brought into contact with the solid adsorbent for a contact time of up to 60 minutes.

[11] 1,1,3,3,3-Pentafluoropropene having a purity of 99.9% or more.

[12] 1,1,3,3,3-Pentafluoropropene containing, as an impurity, tetrafluoropropene in an amount of 0 to 100 ppm.

Advantageous Effects of Invention

According to the purification method for a fluoroolefin having a structure of $=CF_2$ or $=CHF$ of the present invention, it is possible to enhance the purity of the fluoroolefin having a structure of $=CF_2$ or $=CHF$ by removing haloalkane, haloalkene, and/or haloalkyne impurities, in particular, haloalkane, haloalkene, and/or haloalkyne impurities bonded with a chlorine atom or a fluorine atom. Moreover, according to the production method of the present invention, it is possible to obtain a high-purity fluoroolefin through the above-mentioned purification of a fluoroolefin.

DESCRIPTION OF EMBODIMENTS

<Action>

Figure 1:
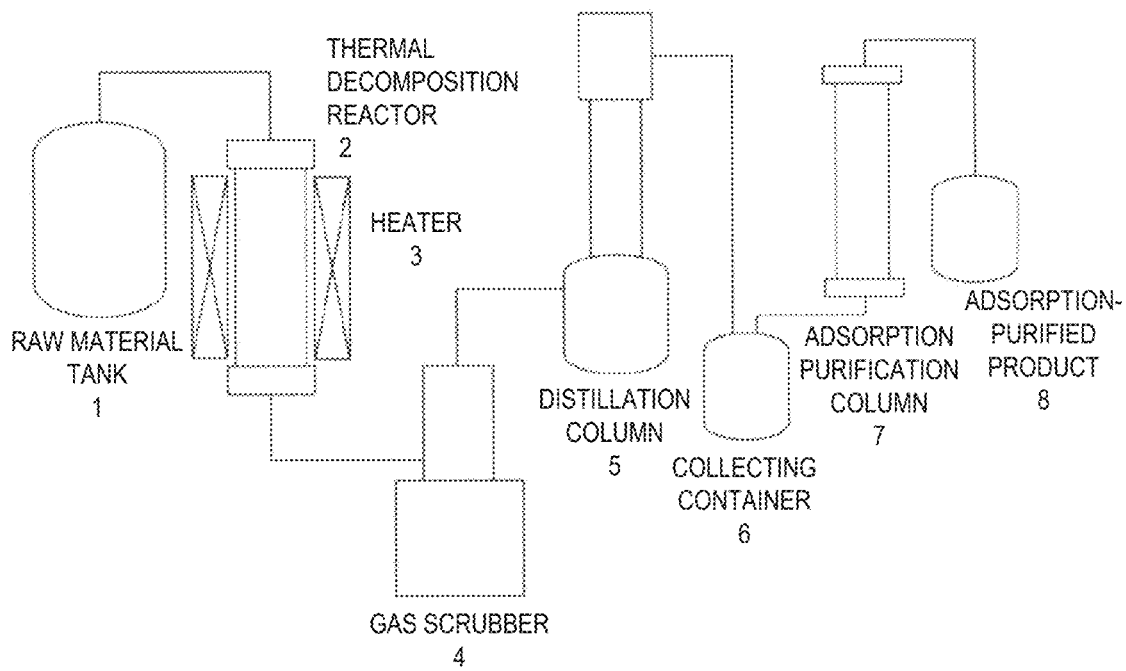
FIG. 1 is a schematic view of an exemplary apparatus for carrying out the purification method of the present invention.

The present invention provides a purification method and a production method for a fluoroolefin having a structure of $=CF_2$ or $=CHF$, characterized by bringing a fluoroolefin having a structure of $=CF_2$ or $=CHF$ that has been obtained by a dehydrohalogenation reaction and that contains at least one of haloalkane, haloalkene, and/or haloalkyne impurities, especially, haloalkane, haloalkene, and/or haloalkyne impurities bonded with a chlorine atom or a fluorine atom into contact with a solid adsorbent to remove the impurities through adsorption. The feature of the present invention is that the purification target is a fluoroolefin having a structure of $=CF_2$ or $=CHF$. A fluoroolefin having a structure of $=CF_2$ or $=CHF$ tends to form many impurities through thermal decomposition compared with fluoroolefins having a structure of $=CH_2$ (above-mentioned 1243zf, 1234yf, and so forth). Meanwhile, the production of such a fluoroolefin having a high purity has not been examined sufficiently in the prior art documents. Accordingly, it was surprising that the production of a high-purity fluoroolefin having a structure of $=CF_2$ or $=CHF$ was made possible through the studies by the present inventors. More specifically, it is possible to obtain high-purity (particularly a purity of 99.9% or more) 1,1,3,3,3-pentafluoropropene by preferentially removing impurities that are difficult to separate by using a distillation column with the theoretical stage number of 40, especially, C3 compounds having a small difference in boiling point. According to the present invention, 1,3,3,3-tetrafluoropropene, which is particularly difficult to separate through distillation and hence is a main impurity, is not detected by allowing to pass through an adsorption column.

Hereinafter, the embodiments of the present invention will be described.

<Purification Method for Fluoroolefins>

A first embodiment of the present invention is a purification method for a fluoroolefin by removing haloalkane, haloalkene, and haloalkyne impurities from a fluoroolefin having a structure of $=CF_2$ or $=CHF$ that contains at least one of haloalkane, haloalkene, and haloalkyne impurities, especially, haloalkane, haloalkene, and haloalkyne impurities bonded with a chlorine atom or a fluorine atom. The first embodiment is characterized by bringing the fluid into contact with a solid adsorbent.

(Fluoroolefins)

A fluoroolefin to be purified is preferably a fluoroolefin having a carbon number of 3 or 4. Specific examples include hexafluoropropene, pentafluoropropene, tetrafluoropropene, trifluoropropene, octafluorobutene, hexafluorobutene, and tetrafluorobutadiene. This means that a mixture containing one or more fluoroolefins selected from the group consisting of these compounds is purified in the present invention. Here, examples of pentafluoropropene include 1,1,2,3,3-pentafluoropropene and 1,1,3,3,3-pentafluoropropene. Examples of tetrafluoropropene include 1,1,3,3-tetrafluoropropene and 1,2,3,3-tetrafluoropropene, and examples of trifluoropropene include 1,3,3-trifluoropropene, 1,1,3-trifluoropropene, and 1,2,3-trifluoropropene. Examples of octafluorobutene include octafluoro-1-butene. Examples of hexafluorobutene include 1,1,3,3,4,4,4-hexafluoro-1-butene and 1,2,3,3,4,4,4-hexafluoro-1-butene. Examples of tetrafluorobutadiene include 1,1,4,4-tetrafluoro-1,3-butadiene.

The fluoroolefin in the present invention may be a reaction product obtained by a synthetic reaction that involves thermal decomposition under high-temperature conditions, especially at 400° C. to 1000° C. Examples of such a synthetic reaction include a reaction of thermally decomposing 1,1,1,3,3,3-hexafluoropropane at a temperature of 400° C. to 1000° C., and more specific examples include the following.

(1) A reaction of thermally decomposing 1,1,1,3,3,3-hexafluoropropane within a hollow reaction tube made of metal, such as nickel. Hastelloy, Monel, or Inconel, at a temperature of 600° C. to 1000° C.

(2) A reaction of thermally decomposing 1,1,1,3,3,3-hexafluoropropane within a reaction tube made of metal, such as nickel or Hastelloy, and filled with metallic filler, such as nickel, at a temperature of 600° C. to 1000° C.

(3) A reaction of thermally decomposing 1,1,1,3,3,3-hexafluoropropane within a reaction tube made of metal, such as nickel or Hastelloy, and filled with a metal catalyst, such as $CrF_3/C$, $AlF_3/C$, $RuF/C$, or $PtF_2/C$, at a temperature of 400° C. to 800° C.

The reaction product, after removing impurities in advance through distillation, is desirably subjected to the purification method of the present invention.

(Haloalkane Impurities)

Haloalkane impurities contained in the above-mentioned fluoroolefin and to be removed in the present invention are preferably haloalkanes having a carbon number of 1, 2, or 3. Moreover, haloalkanes having a carbon number of 2 or 3 are more preferable. Specific examples include hydrofluoroethane and hydrofluoropropane, and more specific examples include tetrafluoroethane, pentafluoropropane, and hexafluoropropane.

(Haloalkene Impurities)

Exemplary haloalkene impurities contained in the above-mentioned fluoroolefin and to be removed in the present invention include, as pentafluoropropene, (Z)-1,2,3,3,3-pentafluoropropene and (E)-1,2,3,3,3-pentafluoropropene; as tetrafluoropropene, 1,3,3,3-tetrafluoropropene; as trifluoropropene, 3,3,3-trifluoropropene; as octafluorobutene, octafluoro-2-butene; as hexafluorobutene, 1,1,1,4,4,4-hexafluoro-2-butene, 2,3,3,4,4,4-hexafluoro-1-butene, and 2-(trifluoromethyl)-3,3,3-trifluoro-1-propene.

(Haloalkyne Impurities)

Exemplary haloalkyne impurities contained in the above-mentioned fluoroolefin and to be removed in the present invention include, as trifluoropropyne, 1,3,3-trifluoropropyne and 3,3,3-trifluoropropyne; and as hexafluorobutyne, 1,1,1,4,4,4-hexafluoro-2-butyne.

(Solid Adsorbents)

Exemplary solid adsorbents in the present invention include activated carbon, zeolites of type A or type X, activated alumina, and silica gel. Among these, zeolites are preferable in view of impurity removal. Cationic species of zeolites are preferably potassium ions, sodium ions, or calcium ions. Exemplary zeolites include zeolite MS-3A (effective pore size of 3 Å, type KA), zeolite MS-4A (effective pore size of 4 Å, type NaA), zeolite MS-5A (effective pore size of 5 Å, type CaA), and zeolite MS-13X (effective pore size of 10 Å, type NaA). The effective pore size of the solid adsorbent is preferably 3 to 50 Å, more preferably 3 to 20 Å, and further preferably 5 to 10 Å.

Before used for purification, a solid adsorbent is preferably subjected to heating treatment with a drying gas (nitrogen gas, in particular) at 100° C. to 350° C. or heating treatment within a container under reduced pressure at 100° C. to 350° C. Consequently, the solid adsorbent is activated to enhance efficiency in impurity removal.

(Contact Between Fluoroolefin and Solid Adsorbent)

The pressure conditions when a fluoroolefin is brought into contact with a solid adsorbent are not particularly limited, but atmospheric pressure to 0.5 MPa (gauge pressure) is commonly adopted. The temperature conditions are preferably 0° C. to 200° C. and more preferably 0° C. to 100° C. As the contact time between a solid adsorbent and a mixed gas becomes longer, the adsorption efficiency of a solid adsorbent increases and a high-purity fluoroolefin is readily obtained. Meanwhile, as the contact time becomes shorter, the processing capacity increases, thereby making efficient purification of a fluoroolefin possible.

In view of efficiency in removal of haloalkane, haloalkene, and haloalkyne impurities, the total content of haloalkane, haloalkene, and haloalkyne impurities contained in a fluoroolefin before purification is preferably 10 mass % or less, more preferably 5 mass % or less, and most preferably 1 mass % or less.

(Purification Apparatus)

Exemplary materials of a purification apparatus include corrosion-resistant metals, such as stainless steel, Inconel, Monel, Hastelloy, and nickel.

FIG. 1 illustrates an exemplary purification apparatus applicable to the present invention. In FIG. 1, a thermal decomposition reactor 2 is a cylindrical tube of nickel, and a heater 3 is disposed around the circumference of the reactor 2 to heat the entire reactor 2 uniformly. In FIG. 1, the reactor 2 is disposed with the cylindrical tube standing vertically, and a raw material gas from a raw material tank 1 is designed to pass through a pipe and then the inside of the reactor 2 from the top to the bottom of the reactor 2. A gas scrubber 4 is disposed downstream of the reactor 2 to remove by-products, such as hydrogen halides and high-boiling compounds formed by thermal decomposition reactions. A distillation column 5 is disposed downstream of the gas scrubber 4 to remove low-boiling compounds and high-boiling compounds through distillation. A purified product that has passed through the distillation column 5 and that contains impurities is kept within a collecting container 6. An adsorption purification column 7 is disposed downstream of the collecting container 6. A difference in processing speed between the distillation column 5 and the adsorption purification column 7 is designed to be absorbed by the collecting container 6. The adsorption purification column 7 is disposed with the nickel cylindrical tube, the inside of which is filled with a solid adsorbent, standing vertically. The purified product containing impurities from the collecting container 6 is designed to pass through a pipe and then the inside of the adsorption purification column 7 from the bottom to the top. The impurities that are difficult to separate through distillation are removed by the solid adsorbent within the adsorption purification column 7, and the resulting adsorption-purified product is collected in a purified product reservoir 8.

Figure 2:
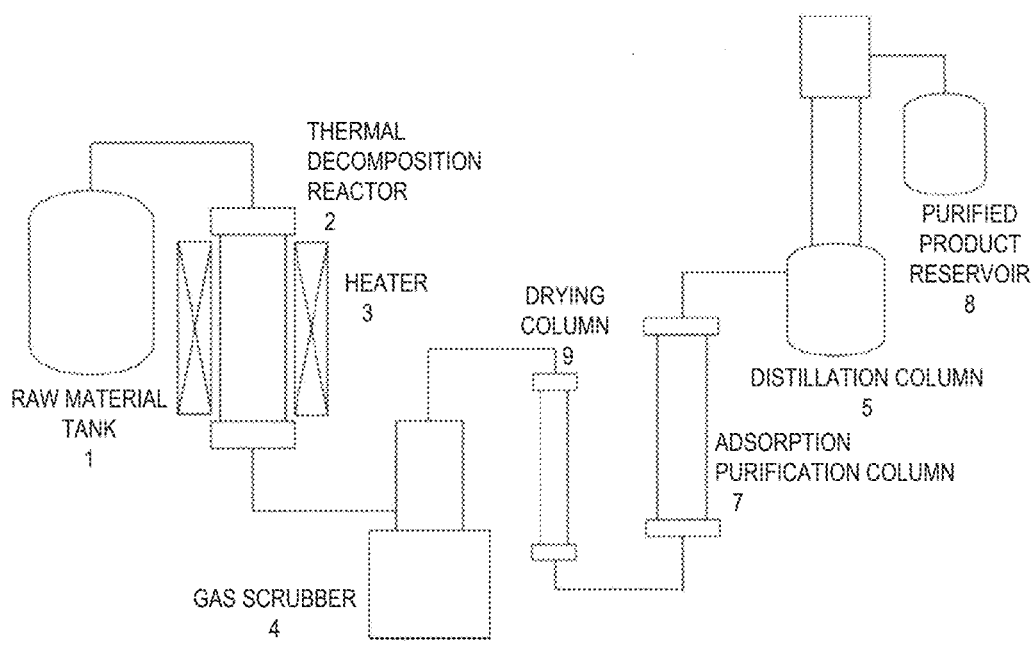
FIG. 2 is a schematic view of another exemplary apparatus for carrying out the purification method of the present invention.

FIG. 2 illustrates another exemplary purification apparatus applicable to the present invention. FIG. 2 differs from FIG. 1 in that a crude product that has passed through a gas scrubber 4 passes through, after moisture removal at a drying column 9, an adsorption purification column 7 first and then is distilled at a distillation column 5, and the resulting adsorption-purified product is collected in a purified product reservoir 8. This means that the purification apparatus of FIG. 2 separates in advance, at the adsorption purification column 7, the impurities that cannot be separated at the distillation column 5. Since the solid adsorbent tends to adsorb moisture and thus lower adsorption efficiency, it is desirable to dispose the drying column 9 upstream of the adsorption purification column 7.

(Production Method and Product of Present Invention)

The present invention also provides a method of producing a high-purity fluoroolefin having a structure of $=CF_2$ or $=CHF$, comprising bringing a fluoroolefin having a structure of $=CF_2$ or $=CHF$ that has been obtained by a dehydrohalogenation reaction and that contains at least one of haloalkane, haloalkene, and haloalkyne impurities, in particular, haloalkane, haloalkene, and haloalkyne impurities bonded with a chlorine atom or a fluorine atom into contact with a solid adsorbent to remove the impurities through adsorption.

The step of bringing a fluoroolefin into contact with a solid adsorbent performed in the production method of the present invention is as described above for the purification method of the present invention. By the production method of the present invention, a fluoroolefin having a high purity, especially, an impurity concentration after purification of 100 ppm or less and, in particular, 0 to 10 ppm is provided. In the dehydrohalogenation reaction, many impurities (in particular, total impurity content of more than 0 ppm and 10 mass % or less) are formed in addition to the target product. According to the production method of the present invention, it is possible to obtain a high-purity fluoroolefin, such as 1,1,3,3,3-pentafluoropropene containing, as an impurity, tetrafluoropropene in an amount of 0 to 100 ppm. A fluoroolefin obtained by the production method of the present invention has a purity of 99% or more, particularly 99.5% or more, particularly 99.9% or more, and particularly 99.99% or more. To the best of the knowledge of the applicant, a fluoroolefin having such a high purity has not been obtained by conventional methods.

EXAMPLES

Hereinafter, the present invention will be described in further detail by means of Examples and a Comparative Example. However, the present invention is by no means limited thereto. Hereinafter, the composition of a mixture was obtained from GC area % by a gas chromatograph (GC-MS or GC-FID).

Comparative Example 1

<Production Method for Fluoropropene>

Into a nickel tube of 3B×1500 mm heated to 800° C. by a resistance heating device, 1,1,1,3,3,3-hexafluoropropane as a raw material was introduced at a flow rate of 9.0 SLM. A gas obtained from the reactor outlet was treated with pure water and an alkaline aqueous solution to yield a mixture of 1,1,3,3,3-pentafluoropropene and impurities shown in Table 1.

The mixture was rectified at a rectification column with the theoretical stage number of 40 to yield a composition shown in Table 1, in other words, a purified product of 1,1,3,3,3-pentafluoropropene having a purity of 98.25% and containing, as impurities, 0.04% of 1,1,1-trifluoroethane, 0.26% of 1,1,1,2-tetrafluoroethane, 0.11% of 3,3,3-trifluoropropene, 0.41% of (Z)-1,2,3,3,3-pentafluoropropene, 0.05% of (E)-1,2,3,3,3-pentafluoropropene, 0.52% of (E)-1,3,3,3-tetrafluoropropene, and 0.37% of 1,1,1,3,3,3-hexafluoropropane.

Example 1

An adsorption purification column was prepared by enclosing 27.6 g of zeolite MS-3A (Zeolum A-3, 4-8 mesh, from Tosoh Corporation) as a solid adsorbent within a SUS 304 tube of ø12A×500 mm and drying with heated nitrogen at an internal temperature of 100° C. for 12 hours. The purified product of 1,1,3,3,3-pentafluoropropene having a purity of 98.25% and containing impurities obtained in Comparative Example 1 was introduced into the adsorption purification column, and the gas composition before introduction was compared with the gas composition obtained after processing at the adsorption purification column. 1,1,3,3,3-Pentafluoropropene obtained from the adsorption purification column contained 0.02% of 1,1,1-trifluoroethane, 0.08% of 1,1,1,2-tetrafluoroethane, 0.02% of 3,3,3-trifluoropropene, 0.15% of (Z)-1,2,3,3,3-pentafluoropropene, 0.02% of (E)-1,2,3,3,3-pentafluoropropene, and 0.19% of 1,1,1,3,3,3-hexafluoropropane and thus had a purity of 99.52%.

Example 2

An adsorption purification column was prepared by enclosing 25.6 g of zeolite MS-4A (Zeolum A-4, 4-8 mesh, from Tosoh Corporation) as a solid adsorbent within a SUS 304 tube of ø12A×500 mm and drying with heated nitrogen at an internal temperature of 100° C. for 12 hours. The purified product of 1,1,3,3,3-pentafluoropropene having a purity of 98.25% and containing impurities obtained in Comparative Example 1 was introduced into the adsorption purification column, and the gas composition before introduction was compared with the gas composition obtained after processing at the adsorption purification column. 1,1,3,3,3-Pentafluoropropene obtained from the adsorption purification column contained 0.26% of (Z)-1,2,3,3,3-pentafluoropropene and thus had a purity of 99.74%.

Example 3

An adsorption purification column was prepared by enclosing 24.8 g of zeolite MS-5A (Zeolum A-5, 4-8 mesh, from Tosoh Corporation) as a solid adsorbent within a SUS 304 tube of ø12A×500 mm and drying with heated nitrogen at an internal temperature of 100° C. for 12 hours. The purified product of 1,1,3,3,3-pentafluoropropene having a purity of 98.25% and containing impurities obtained in Comparative Example 1 was introduced into the adsorption purification column, and the gas composition before introduction was compared with the gas composition obtained after processing at the adsorption purification column. 1,1,3,3,3-Pentafluoropropene obtained from the adsorption purification column contained 0.04% of 1,1,1-trifluoroethane, 0.06% of 1,1,1,2-tetrafluoroethane, 0.06% of 3,3,3-trifluoropropene, 0.23% of (Z)-1,2,3,3,3-pentafluoropropene, and 0.13% of 1,1,1,3,3,3-hexafluoropropane and thus had a purity of 99.48%.

Example 4

An adsorption purification column was prepared by enclosing 25.6 g of zeolite MS-13X (Zeolum F-9, 4-8 mesh, from Tosoh Corporation) as a solid adsorbent within a SUS 304 tube of ø12A×500 mm and drying with heated nitrogen at an internal temperature of 100° C. for 12 hours. The purified product of 1,1,3,3,3-pentafluoropropene having a purity of 98.25% and containing impurities obtained in Comparative Example 1 was introduced into the adsorption purification column, and the gas composition before introduction was compared with the gas composition obtained after processing at the adsorption purification column. 1,1,3,3,3-Pentafluoropropene obtained from the adsorption purification column contained 0.02% of 1,1,1-trifluoroethane and thus had a purity of 99.98%.

Example 5

An adsorption purification column was prepared by enclosing 23.7 g of activated alumina (grade D activated alumina, 2-5 mm, from Axens SA) as a solid adsorbent within a SUS 304 tube of ø12A×500 mm and drying with heated nitrogen at an internal temperature of 100° C. for 12 hours. The purified product of 1,1,3,3,3-pentafluoropropene having a purity of 98.25% and containing impurities obtained in Comparative Example 1 was introduced into the adsorption purification column, and the gas composition before introduction was compared with the gas composition obtained after processing at the adsorption purification column. 1,1,3,3,3-Pentafluoropropene obtained from the adsorption purification column contained no impurity and thus had a purity of 100%.

TABLE 1

| % | Comp. Ex. 1 | Ex. 1 | Ex. 2 | Ex. 3 | Ex. 4 | Ex. 5 |
|---|---|---|---|---|---|---|
| $CF_3-CH_3$ | 0.04 | 0.02 | — | 0.04 | 0.02 | — |
| $CF_3-CH_2F$ | 0.26 | 0.08 | — | 0.06 | — | — |
| $CF_3-CH=CH_2$ | 0.11 | 0.02 | — | 0.06 | — | — |
| (Z)-$CF_3-CF=CHF$ | 0.41 | 0.15 | 0.26 | 0.23 | — | — |
| (E)-$CF_3-CF=CHF$ | 0.05 | 0.02 | — | — | — | — |
| (E)-$CF_3-CH=CHF$ | 0.52 | — | — | — | — | — |
| $CF_3-CH_2-CF_3$ | 0.37 | 0.19 | — | 0.13 | — | — |
| $CF_3-CH=CF_2$ | 98.25 | 99.52 | 99.74 | 99.48 | 99.98 | 100 |

As shown in Table 1, it is possible according to the present invention to remove haloalkanes and/or haloolefins significantly, thereby enhancing the purity of a purification target to 99% or more. In particular, when alumina or a zeolite having an effective pore size of 10 Å was used, impurities were removed effectively and remarkably (Examples 4 and 5). According to the present invention, it is possible to preferentially remove impurities that are difficult to separate by using a distillation column with the theoretical stage number of 40, especially, C3 compounds having a small difference in boiling point and thus to obtain high-purity 1,1,3,3,3-pentafluoropropene. In the present invention, 1,3,3,3-tetrafluoropropene, which is particularly difficult to separate through distillation and hence is a main impurity, is not detected by allowing to pass through an adsorption column.

The invention claimed is:

1. A method of purifying 1,1,3,3,3-pentafluoropropene, comprising bringing a fluid containing 1,1,3,3,3-pentafluoropropene that has been obtained by a dehydrohalogenation reaction and that contains at least one of impurities consisting of:

$CF_3-CH_3$;

$CF_3-CH_2F$;

$CF_3-CH=CH_2$;

(Z)—$CF_3-CF=CHF$;

(E)—$CF_3-CF=CHF$;

(E)—$CF_3-CH=CHF$; and $CF_3-CH_2-CF_3$, into contact with a solid adsorbent to remove the impurities through adsorption.

2. The method according to claim 1, wherein the solid adsorbent has an effective pore size of 3 to 50 Å.

3. The method according to claim 1, wherein the solid adsorbent is at least one selected from the group consisting of activated carbon, molecular sieves of type A or type X, and activated alumina.

4. The method according to claim 1, wherein the total content of the impurities in the fluid containing 1,1,3,3,3-pentafluoropropene is more than 0 ppm and 10 mass % or less.

5. The method according to claim 1, wherein the fluid containing 1,1,3,3,3-pentafluoropropene is brought into contact with the solid adsorbent for a contact time of up to 60 minutes.

6. The method according to claim 1, wherein the solid adsorbent is activated alumina.

7. A method of producing 1,1,3,3,3-pentafluoropropene having a purity of 99% or more, comprising bringing a fluid containing 1,1,3,3,3-pentafluoropropene that has been obtained by a dehydrohalogenation reaction and that contains at least one of impurities consisting of:

$CF_3-CH_3$;

$CF_3-CH_2F$;

$CF_3-CH=CH_2$;

(Z)—$CF_3-CF=CHF$;

(E)—$CF_3-CF=CHF$;

(E)—CF$_3$—CH=CHF; and

CF$_3$—CH$_2$—CF$_3$, into contact with a solid adsorbent to remove the impurities through adsorption.

8. The method according to claim 7, wherein the solid adsorbent has an effective pore size of 3 to 50 Å.

9. The method according to claim 7, wherein the solid adsorbent is at least one selected from the group consisting of activated carbon, molecular sieves of type A or type X, and activated alumina.

10. The method according to claim 7, wherein the total content of the impurities in the fluid containing 1,1,3,3,3-pentafluoropropene is more than 0 ppm and 10 mass % or less.

11. The method according to claim 7, wherein the fluid containing 1,1,3,3,3-pentafluoropropene is brought into contact with the solid adsorbent for a contact time of up to 60 minutes.

12. The method according to claim 7, wherein the solid adsorbent is activated alumina.

* * * * *